United States Patent [19]

Taylor et al.

[11] Patent Number: 5,785,952
[45] Date of Patent: *Jul. 28, 1998

[54] AEROSOL MEDICAMENT FORMULATION HAVING A SURFACE COATING OF SURFACTANT

[75] Inventors: Anthony James Taylor; Patricia Kwon Phieu Burnell, both of Ware, Great Britain

[73] Assignee: Glaxo Group Limited, Greenford, England

[*] Notice: The term of this patent shall not extend beyond the expiration date of Pat. No. 5,658,549.

[21] Appl. No.: 440,441

[22] Filed: May 12, 1995

Related U.S. Application Data

[63] Continuation of Ser. No. 305,816, Sep. 14, 1994, abandoned, which is a continuation of Ser. No. 39,425, filed as PCT/GB91/01961 published as WO92/08447, abandoned.

[30] Foreign Application Priority Data

Nov. 9, 1990 [GB] United Kingdom ............... 9024366

[51] Int. Cl.$^6$ .................................................. A61K 9/12
[52] U.S. Cl. .................................................. 424/46; 424/45
[58] Field of Search .............................. 424/46, 45, 47

[56] References Cited

U.S. PATENT DOCUMENTS

| | | | |
|---|---|---|---|
| 2,868,691 | 1/1959 | Porush et al. | 424/45 |
| 2,885,427 | 5/1959 | Ruh et al. | 424/45 |
| 3,219,533 | 11/1965 | Mullins | 424/45 |
| 3,897,779 | 8/1975 | Hansen | 424/45 |
| 4,352,789 | 10/1982 | Thiel . | |
| 5,118,494 | 6/1992 | Schultz et al. | 424/45 |
| 5,126,123 | 6/1992 | Johnson | 424/45 |
| 5,225,183 | 7/1993 | Purewal et al. | 424/45 |
| 5,230,884 | 7/1993 | Evans et al. | 424/45 |
| 5,348,730 | 9/1994 | Greenleaf et al. | 424/45 |
| 5,605,674 | 2/1997 | Purewal et al. | 424/45 |
| 5,653,962 | 8/1997 | Akehurst et al. | 424/45 |
| 5,658,549 | 8/1997 | Akehurst et al. | 424/45 |
| 5,674,471 | 10/1997 | Akehurst et al. | 424/45 |
| 5,674,473 | 10/1997 | Purewal et al. | 424/45 |
| 5,681,545 | 10/1997 | Purewal et al. | 424/45 |
| 5,695,743 | 12/1997 | Purewal et al. | 424/45 |

FOREIGN PATENT DOCUMENTS

| | | |
|---|---|---|
| 452384 | 10/1993 | European Pat. Off. . |
| 1719443 | 4/1972 | Germany . |
| 3905726 | 8/1990 | Germany . |
| 977934 | 12/1994 | United Kingdom . |
| 86/04233 | 7/1986 | WIPO . |
| 90/07333 | 7/1990 | WIPO . |
| 91/04011 | 4/1991 | WIPO . |
| 91/14422 | 10/1991 | WIPO . |
| 92/00061 | 1/1992 | WIPO . |
| 92/00062 | 1/1992 | WIPO . |
| 92/00107 | 1/1992 | WIPO . |

OTHER PUBLICATIONS

Voigt, Manual of Pharmaceutical Technology, 5th Ed., pp. 359–370 (1984).

Lachman et al. Eds. *The Theory and Practice of Industrial Pharmacy*, 2nd Ed., pp. 270 and 276–280 (1976).

Evans et al., *Journal of Pharmacy and Pharmacology*, 40 (1988), 7P.

Clarke et al. *Journal of Pharmacy and Pharmacology*, Supplement 42 (1990), 9P.

"Hoechst on the substitution for FCKW" Position:Hoechst Chemikalien. (1990).

Meirion Jones, *New Scientist*, pp. 56–60, (1988).

Lachman et al., Eds., The Theory and Practice of Industrial Pharmacy, 3rd Ed., pp. 603–604, (1986).

*Primary Examiner*—Raj Bawa
*Attorney, Agent, or Firm*—Bacon & Thomas

[57] ABSTRACT

The present application is directed to aerosol formulations comprising (1) a medicament which is selected from the group consisting of salmeterol, fluticasone esters, 4-amino-3,5-dichloro-α-[[[6-[2-(2-pyridinyl)ethoxy]hexyl]amino]methyl]benzenemethanol and physiologically acceptable salts and solvates thereof in particulate form and having a surface coating of a surfactant, and (2) a hydrogen-containing fluorocarbon or chlorofluorocarbon propellant. The invention also describes methods for preparation of these aerosol formulations.

19 Claims, No Drawings

AEROSOL MEDICAMENT FORMULATION HAVING A SURFACE COATING OF SURFACTANT

CROSS-REFERENCE TO RELATED APPLICATIONS

The present application is a continuation of application Ser. No. 08/305,816, filed Sep. 14, 1994, now abandoned, which is a continuation of application Ser. No. 08/039,425, filed Apr. 29, 1993, now abandoned, which is the U.S. national phase of international application number PCT/GB91/01961, filed Nov. 7, 1991.

BACKGROUND OF THE INVENTION

1. Field of the Invention

This invention relates to aerosol formulations of use in the administration of medicaments by inhalation.

2. Description of the Prior Art

The use of aerosols to administer medicaments has been known for several decades. Such aerosols generally comprise the medicament, one or more chlorofluorocarbon propellants and either a surfactant or a solvent, such as ethanol.

The most commonly used aerosol propellants for medicaments have been Freon 11 ($CCl_3F$) in admixture with Freon 12 ($CCl_2F_2$) and Freon 114 ($CF_2Cl.CF_2Cl$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise hydrogen-containing chlorofluorocarbons and fluorocarbons; medicinal aerosol formulations using such propellant systems are disclosed in, for example, EP 0372777. EP 0372777 requires the use of 1,1,1,2-tetrafluoroethane in combination with both a cosolvent having greater polarity than 1,1,1,2-tetrafluoroethane (e.g. an alcohol or a lower alkane) and a surfactant in order to achieve a stable formulation of a medicament powder. In particular it is noted in the specification at page 3, line 7 that "it has been found that the use of Propellant 134a (1,1,1,2-tetrafluoroethane) and drug as a binary mixture or in combination with a conventional surfactant such as sorbitan trioleate does not provide formulations having suitable properties for use with pressurised inhalers".

SUMMARY OF THE INVENTION

We have now surprisingly found that, in contradistinction to this teaching, it is in fact possible to obtain stable dispersions of certain finely-powdered medicaments together with certain surfactants in hydrogen-containing fluorocarbon or chlorofluorocarbon propellants such as 1,1,1,2-tetrafluoroethane if the surfactant is present as a dry coating on the particles of medicament. More particularly, such stable dispersions may be formed where the medicament is selected from salmeterol, fluticasone esters, 4-amino-3,5-dichloro-α-[[[6-[2-(2-pyridinyl)ethoxy]hexyl]amino]methyl]benzenemethanol, and physiologically acceptable salts and solvates thereof. This is in contrast to the procedure of EP 0372777, where the medicament and surfactant are simultaneously homogenised, e.g. in ethanol, prior to addition of the propellant.

There is thus provided an aerosol formulation comprising (A) a medicament selected from the group comprising salmeterol, fluticasone esters, 4-amino-3,5-dichloro-α-[[[6-[2-(2-pyridinyl)ethoxy]hexyl]amino]methyl]benzenemethanol, and physiologically acceptable salts and solvates thereof in particulate form and having a surface-coating of a surfactant; and (B) a hydrogen-containing fluorocarbon or chlorofluorocarbon propellant.

The propellants for use in the invention may be any hydrogen-containing fluorocarbon or chlorofluorocarbon or mixtures thereof having a sufficient vapour pressure to render them effective as propellants. Such propellants include for example $C_{1-4}$ hydrogen-containing fluorocarbons and chlorofluorocarbons such as $CH_2ClF$, $CClF_2$—$CHClF$, $CF_3$—$CHClF$, $CHF_2$—$CClF_2$, $CHClF$—$CHF_2$, $CF_3$—$CH_2Cl$, $CHF_2$—$CHF_2$, $CF_3$—$CH_2F$, $CClF_2$—$CH_3$, $CHF_2$—$CH_3$ and $CF_3CHFCF_3$.

Where mixtures of the hydrogen-containing fluorocarbons or chlorofluorocarbons are employed they may be mixtures of the above identified compounds or mixtures, preferably binary mixtures, with other hydrogen-containing fluorocarbons or chlorofluorocarbons for example $CHClF_2$, $CH_2F_2$ and $CF_3CH_3$.

The propellant may additionally contain a volatile saturated hydrocarbon for example n-butane, isobutane, pentane and isopentane. Preferably a single hydrogen-containing fluorocarbon or chlorofluorocarbon is employed as the propellant Preferably the propellant will be a non-solvent for the medicament. Particularly preferred as propellants are 1,1,1,2-tetrafluoroethane ($CF_3.CH_2F$) and 1,1,1,2,3,3,3-heptafluoro-n-propane ($CF_3.CHF.CF_3$).

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

It is further desirable that the formulations of the invention are substantially free of liquid components of higher polarity than the propellant employed. In particular formulations which are free of alcohols such as ethanol are preferable.

Polarity may be determined for example, by the method described in European Patent Application Publication No. 0327777.

As used herein "substantially free" means less than 1% w/w based upon the hydrogen-containing fluorocarbon or chlorofluorocarbons in particular less than 0.5% for example 0.1% or less.

Where appropriate the medicaments may be used in the form of salts (e.g. as alkali metal or amine salts or as acid addition salts) or as esters (e.g. lower alkyl esters) to optimise the activity and/or stability of the medicament and/or to minimise the solubility of the medicament in the propellant.

For use in the formulations of the present invention, salmeterol will preferably be in the form of its 1-hydroxy-2-naphthoate salt, the fluticasone ester will preferably be the propionate, and 4-amino-3,5-dichloro-α-[[[6-[2-(2-pyridinyl)ethoxy]hexyl]amino]methyl]benzenemethanol will preferably be in the form of the (R) enantiomer.

The surfactants for use in the invention will have no affinity for the propellant (that is to say they will contain no groups which have affinity with the propellant).

The surfactants must be physiologically acceptable upon administration by inhalation. Surfactants within this category include materials such as benzalkonium chloride, lecithin, oleic acid and sorbitan trioleate (Span [R]85).

The use of substantially non-ionic surfactants which have reasonable solubility in substantially non-polar solvents is frequently advantageous since it facilitates coating of the medicament particles using solutions of surfactant in non-polar solvents in which the medicament has limited or minimal solubility.

Thus according to a further aspect of the invention the surfactant-coated medicament may be prepared by slurrying particulate (e.g. micronised) medicament with a solution of a surfactant such as lecithin in a substantially non-polar solvent (e.g. a lower alkane such as isopentane or a chlorofluorocarbon such as trichlorofluoromethane), optionally homogenising the slurry (e.g. by sonication), removing the solvent and if necessary simultaneously and/or subsequently breaking up the resulting solid cake. The thus-obtained surfactant-coated particulate medicaments are novel and form a further feature of the invention.

The formulations of the invention may be prepared by dispersing the surface-coated medicament, obtained as described above, in the chosen propellant in an appropriate aerosol container, e.g. with the aid of sonication.

The particle size of the finely-powdered medicament should be such as to permit inhalation of substantially all of the medicament into the bronchial system upon administration of the aerosol formulation and will thus be less than 100 microns, desirably less than 20 microns, and preferably in the range 2–10 microns, e.g. 2–5 microns.

The amount of surfactant employed in coating the particulate medicament is desirably in the range 0.01–10.0% w/w, preferably 0.05–5.0% w/w, relative to the medicament, and may advantageously be chosen such that a substantially monomolecular coating of surfactant is formed. The final aerosol formulation desirably contains 0.005–5.0% w/w, preferably 0.01–1.0% w/w, of coated medicament relative to the total weight of the formulation.

The following non-limitative Examples serve to illustrate the invention.

EXAMPLE 1

(A) Preparation of Lecithin-coated Salmeterol Hydroxynaphthoate (a) Lecithin (Epikuron 145V-3.65 mg) was dissolved in a small amount of isopentane and the resulting solution was added to micronised salmeterol hydroxynaphthoate (0.5 g). Further isopentane (7.0 g total) was added to form a slurry, which was sonicated for 3 minutes. The resulting suspension was dried by evaporating the isopentane at ambient temperature in a fume cupboard, whereafter the resulting dried plug was roughly broken up and then dried further in a vacuum oven. The thus-obtained product was further broken up using a mortar and pestle to yield lecithin-coated salmeterol hydroxynaphthoate containing 0.73% w/w of lecithin relative to the salmeterol hydroxynaphthoate.

(b) The above procedure was repeated except that 6.10 mg of lecithin was employed, whereby a coated product containing 1.22% w/w of lecithin relative to the salmeterol hydroxynaphthoate was obtained.

(c) The above procedure was again repeated except that 7.80 mg of lecithin was employed, thereby yielding a coated product containing 1.56% w/w of lecithin relative to the salmeterol hydroxynaphthoate.

(B) Formulation of Lecithin-coated Salmeterol Hydroxynaphthoate in 1,1,1,2-Tetrafluoroethane Samples of each of the products of Example 1A (a)–(c) (9.1 mg) were weighed into aerosol cans. 1,1,1,2-Tetrafluoroethane (18.2 g–99.5% w/w of total fill weight) was added to each can, whereafter suitable metering valves were crimped onto the cans, which were then each sonicated for 5 minutes. The resulting aerosols contained salmeterol in an amount equivalent to 240 actuations at 25 µg per actuation.

EXAMPLE 2

(A) Preparation of lecithin -coated fluticasone propionate

Lecithin (Epikuron 145V-2.5 mg) was dissolved in a small amount of isopentane and the resulting solution was added to micronised fluticasone propionate (0.5 g). Further isopentane (20 ml) was added to form a slurry, which was sonicated for 3 minutes. The resulting suspension was dried by evaporating the isopentane at ambient temperature in a fume cupboard, whereafter the resulting dried plug was roughly broken up and then dried further in a vacuum oven. The thus-obtained product was further broken up using a mortar and pestle to yield lecithin-coated fluticasone propionate containing 0.5% $^w/_w$ of lecithin relative to the fluticasone propionate.

(B) Formulation of lecithin-coated fluticasone propionate in 1,1,1,2-tetrafluoroethane A sample of the product of Example 2(A) (9.1 mg) was weighed into aerosol cans. 1,1,1,2-Tetrafluoroethane (18.2 g-99.5% w/w of total fill weight) was added to each can, whereafter suitable metering valves were crimped onto the cans, which were then each sonicated for 5 minutes. The resulting aerosols contained fluticasone propionate in an amount equivalent to 240 actuations at 25 µg per actuation.

EXAMPLE 3

(A) Preparation of Oleic Acid-coated Salmeterol Hydroxynaphthoate

Oleic acid (10 mg) was dissolved in a small amount of isopentane and the resulting solution was added to micronised salmeterol hydroxynaphthoate (1.0 g). Further isopentane (25 ml total) was added to form a slurry, which was sonicated for 3 minutes. The resulting suspension was dried by evaporating the isopentane at ambient temperature in a fume cupboard, whereafter the resulting dried plug was roughly broken up and then dried further in a vacuum oven. The thus-obtained product was further broken up using a mortar and pestle to yield oleic acid-coated salmeterol hydroxynaphthoate containing 1.0% w/w of oleic acid relative to the salmeterol hydroxynaphthoate.

(B) Formulation of Oleic acid-coated Salmeterol Hydroxynaphthoate in 1,1,1,2-Tetrafluoroethane Samples of the product of Example 3A (9.1 mg) were weighed into aerosol cans. 1,1,1,2-Tetrafluoroethane (18.2 g-99.5% w/w of total fill weight) was added to each can, whereafter suitable metering valves were crimped onto the cans, which were then each sonicated for 5 minutes. The resulting aerosols contained salmeterol in an amount equivalent to 240 actuations at 25 µg per actuation.

EXAMPLE 4

(A) Preparation of Sorbitan Trioleate-coated Salmeterol Hydroxynaphthoate

Sorbitan trioleate (Span 85–10 mg) was dissolved in a small amount of isopentane and the resulting solution was added to micronised salmeterol hydroxynaphthoate (1.0 g). Further isopentane (25 ml total) was added to form a slurry, which was sonicated for 3 minutes. The resulting suspension was dried by evaporating the isopentane at ambient temperature in a fume cupboard, whereafter the resulting dried plug was roughly broken up and then dried further in a vacuum oven. The thus-obtained product was further broken up using a mortar and pestle to yield sorbitan trioleate-coated salmeterol hydroxynaphthoate containing 1.0% w/w of sorbitan trioleate relative to the salmeterol hydroxynaphthoate.

(B) Formulation of Sorbitan Trioleate-coated Salmeterol Hydroxynaphthoate in 1,1,1,2-Tetrafluoroethane Samples of the product of Example 4A (9.1 mg) were weighed into aerosol cans. 1,1,1,2-Tetrafluoroethane (18.2 g–99.5% w/w of total fill weight) was added to each can, whereafter suitable metering valves were crimped onto the cans, which were then each sonicated for 5 minutes. The resulting aerosols contained salmeterol in an amount equivalent to 240 actuations at 25 µg per actuation.

We claim:

1. An aerosol dispersion formulation comprising a hydrogen-containing fluorocarbon or a hydrogen-containing chlorofluorocarbon propellant and a surfactant-coated medicament in an amount of from 0.005 to 5% w/w, based upon the total weight of the formulation, said surfactant-coated medicament consisting of a medicament selected from the group consisting of salmeterol, fluticasone propionate and physiologically acceptable salts and solvates thereof in particulate form, said medicament having a particle size of less than 100 microns and having a dry surface coating of surfactant, which surfactant is present in an amount of from 0.01 to 10% w/w, based upon the weight of the medicament, which surfactant has no affinity for said propellant, and wherein the formulation contains less than 0.5% w/w, based upon the weight of the propellant of liquid components of higher polarity than the propellant.

2. A formulation as claimed in claim 1 wherein the propellant comprises 1,1,1,2-tetrafluoroethane or 1,1,1,2,3,3,3-heptafluoropropane.

3. A formulation as claimed in claim 1 wherein the propellant comprises 1,1,1,2-tetrafluoroethane.

4. A formulation as claimed in claim 1 which contains less than 1% w/w, based upon the hydrogen-containing fluorocarbon or hydrogen-containing chlorofluorocarbon propellant, of hydrogen-containing chlorofluorocarbons.

5. A formulation as claimed in claim 4 which contains less than 0.5% w/w of hydrogen-containing chlorofluorocarbons.

6. A formulation as claimed in claim 4 which contains 0.1% w/w or less of hydrogen-containing chlorofluorocarbons.

7. A formulation as claimed in claim 1 wherein the surfactant is selected from the group consisting of benzalkonium chloride, lecithin, oleic acid and sorbitan trioleate.

8. A formulation as claimed in claim 1 wherein the medicament is salmeterol or a physiologically acceptable salt thereof.

9. A formulation as claimed in claim 1 wherein the medicament is salmeterol in the form of its 1-hydroxy-2-naphthoate salt.

10. A formulation as claimed in claim 9 wherein the propellant is 1,1,1,2-tetrafluoroethane.

11. A formulation as claimed in claim 10 wherein the surfactant is selected from the group consisting of lecithin, oleic acid and sorbitan trioleate.

12. A formulation as claimed in claim 1 wherein the medicament is fluticasone propionate.

13. A formulation as claimed in claim 12 wherein the propellant is 1,1,1,2-tetrafluoroethane.

14. A formulation as claimed in claim 13 wherein the surfactant is selected from the group consisting of lecithin, oleic acid and sorbitan trioleate.

15. An aerosol dispersion formulation consisting essentially of a hydrogen-containing fluorocarbon or a hydrogen-containing chlorofluorocarbon propellant, and a surfactant-coated medicament in an amount of from 0.005 to 5% w/w based upon the total weight of the formulation, said surfactant-coated medicament consisting of a medicament selected from the group consisting of salmeterol, fluticasone propionate and physiologically acceptable salts and solvates thereof in particulate form, said medicament having a particle size of less than 100 microns and having a dry surface coating of surfactant, which surfactant is present in an amount of from 0.01 to 10% w/w based upon the weight of the medicament, and which surfactant has no affinity for said propellant.

16. An aerosol dispersion formulation consisting essentially of 1,1,1,2-fluoroethane or 1,1,1,2,3,3,3-heptafluoropropane as propellant, and a surfactant-coated medicament in an amount of from 0.005 to 5% w/w based upon the total weight of the formulation, said surfactant-coated medicament consisting of a medicament selected from the group consisting of salmeterol, fluticasone propionate, and salts and solvates thereof in particulate form, said medicament having a particle size of less than 100 microns and having a dry surface coating of surfactant, which surfactant is present in an amount of from 0.01 to 10% w/w based upon the weight of the medicament, and which surfactant has no affinity for said propellant.

17. A formulation according to claim 1 which contains no liquid components of higher polarity than the propellant.

18. A formulation according to claim 17, which is free of alcohol.

19. A formulation according to claim 18, which is free of ethanol.

* * * * *